United States Patent
Schnetker et al.

(10) Patent No.: US 8,869,624 B2
(45) Date of Patent: Oct. 28, 2014

(54) IN-SITU MONITORING DEVICE AND METHOD TO DETERMINE ACCUMULATED PRINTED WIRING BOARD VIBRATION STRESS FATIGUE

(75) Inventors: Ted R. Schnetker, Rockford, IL (US); Robert C. Cooney, Janesville, WI (US)

(73) Assignee: Hamilton Sundstrand Corporation, Rockford, IL (US)

( * ) Notice: Subject to any disclaimer, the term of this patent is extended or adjusted under 35 U.S.C. 154(b) by 919 days.

(21) Appl. No.: 12/886,497

(22) Filed: Sep. 20, 2010

(65) Prior Publication Data

US 2011/0005327 A1 Jan. 13, 2011

Related U.S. Application Data

(62) Division of application No. 11/450,629, filed on Jun. 9, 2006, now Pat. No. 7,946,175.

(51) Int. Cl.
| | |
|---|---|
| *G01B 7/16* | (2006.01) |
| *G01R 31/28* | (2006.01) |
| *H05K 1/02* | (2006.01) |
| *G01M 7/02* | (2006.01) |
| *H05K 1/03* | (2006.01) |

(52) U.S. Cl.
CPC .......... *G01R 31/2817* (2013.01); *H05K 1/0393* (2013.01); *G01N 2203/0023* (2013.01); *H05K 1/0271* (2013.01); *G01M 7/025* (2013.01); *H05K 2201/10083* (2013.01); *G01N 2203/0005* (2013.01); *H05K 2201/10151* (2013.01)
USPC ............................................. 73/767; 73/577

(58) Field of Classification Search
CPC .............. G01B 7/16; G01B 7/20; G01B 7/22; H01L 25/00; H01L 27/00
USPC .......... 73/577, 570, 760, 767, 768, 777, 778, 73/763, 774, 775; 438/14, 17, 48
See application file for complete search history.

(56) References Cited

U.S. PATENT DOCUMENTS

| | | | |
|---|---|---|---|
| 4,664,309 A | | 5/1987 | Allen et al. |
| 4,901,575 A | | 2/1990 | Bohannan et al. |
| 5,255,565 A | | 10/1993 | Judd et al. |
| 5,786,621 A | * | 7/1998 | Saif et al. ..................... 257/415 |
| 5,789,682 A | | 8/1998 | Dickinson et al. |
| 5,930,604 A | | 7/1999 | Leonard et al. |
| 5,984,874 A | * | 11/1999 | Cerwin ........................ 600/549 |
| 6,088,474 A | * | 7/2000 | Dudasko et al. .............. 382/145 |
| 6,143,992 A | | 11/2000 | Sato et al. |
| 6,165,885 A | | 12/2000 | Gaynes et al. |
| 6,246,011 B1 | | 6/2001 | Abraham et al. |
| 6,251,766 B1 | | 6/2001 | Desai et al. |
| 6,255,940 B1 | * | 7/2001 | Phelan et al. ................. 340/447 |
| 6,268,568 B1 | | 7/2001 | Kim |

(Continued)

*Primary Examiner* — Peter Macchiarolo
*Assistant Examiner* — Samir M Shah
(74) *Attorney, Agent, or Firm* — Carlson, Gaskey & Olds, P.C.

(57) ABSTRACT

A monitoring system includes a calibrated micro-electro-mechanical structure (MEMS) matrix in communication with a controller. The MEMS matrix includes MEMS elements of various sizes which create a continuum of vibration-stress-resistant elements. The MEMS elements will flex in response to flexing of a printed circuit board due to mechanical vibration until failure occurs. The controller monitors the continuity of the MEMS matrix to determine which elements of the MEMS matrix have failed to accurately determine the accumulated vibration stress experienced by the printed circuit board.

5 Claims, 5 Drawing Sheets

(56) References Cited

U.S. PATENT DOCUMENTS

| | | | |
|---|---|---|---|
| 6,352,516 B1 * | 3/2002 | Pozos et al. | 600/587 |
| 6,424,165 B1 * | 7/2002 | de Boer et al. | 324/750.23 |
| 6,424,667 B1 | 7/2002 | Endriz et al. | |
| 6,452,502 B1 * | 9/2002 | Dishongh et al. | 340/653 |
| 6,501,211 B1 | 12/2002 | Nasrollahzadeh | |
| 6,531,343 B1 | 3/2003 | Carter et al. | |
| 6,567,715 B1 * | 5/2003 | Sinclair et al. | 700/110 |
| 6,586,843 B2 | 7/2003 | Sterritt et al. | |
| 6,590,212 B1 * | 7/2003 | Joseph et al. | 250/311 |
| 6,624,748 B1 * | 9/2003 | Phelan et al. | 340/442 |
| 6,629,448 B1 * | 10/2003 | Cvancara | 73/1.38 |
| 6,671,149 B1 | 12/2003 | Chen, Jr. et al. | |
| 6,759,738 B1 | 7/2004 | Fallon et al. | |
| 6,841,882 B2 | 1/2005 | Chien | |
| 6,953,985 B2 | 10/2005 | Lin et al. | |
| 7,000,821 B2 | 2/2006 | Sterrett et al. | |
| 7,007,606 B1 | 3/2006 | Maurer et al. | |
| 7,014,094 B2 | 3/2006 | Alcoe | |
| 7,015,885 B2 | 3/2006 | Novotny et al. | |
| 7,028,732 B1 * | 4/2006 | Phelan et al. | 152/152.1 |
| 7,170,304 B2 * | 1/2007 | Schaeffer et al. | 324/750.03 |
| 7,377,179 B2 * | 5/2008 | Anderson | 73/767 |
| 7,380,461 B2 * | 6/2008 | Majeti | 73/780 |
| 7,576,901 B2 * | 8/2009 | Chui et al. | 359/290 |
| 7,932,728 B2 * | 4/2011 | Chou et al. | 324/525 |
| 2004/0025595 A1 * | 2/2004 | Brennan | 73/787 |
| 2005/0279177 A1 * | 12/2005 | Hsu et al. | 73/775 |
| 2007/0107530 A1 * | 5/2007 | Anderson | 73/808 |
| 2007/0296068 A1 * | 12/2007 | Schnetker | 257/669 |
| 2007/0299345 A1 * | 12/2007 | Adachi et al. | 600/459 |
| 2012/0137787 A1 * | 6/2012 | Yao et al. | 73/767 |

* cited by examiner

IN-SITU MONITORING DEVICE AND METHOD TO DETERMINE ACCUMULATED PRINTED WIRING BOARD VIBRATION STRESS FATIGUE

REFERENCE TO RELATED APPLICATIONS

The present application is a divisional application of U.S. patent application Ser. No. 11/450,629, filed Jun. 9, 2006 now U.S. Pat. No. 7,946,175.

BACKGROUND OF THE INVENTION

The present invention relates to determining the accumulated vibration stress fatigue of an electronic system, and more particularly to a calibrated micro-electro-mechanical structure (MEMS) which is monitored to determine the accumulated printed wiring board flexure due to mechanical vibration.

During its design life, electronic systems can be exposed to a wide variety of vibration and shock environments. In order to reduce testing time and cost, laboratory tests are typically conducted on electronics in a time-accelerated manner and results extrapolated to the intended application environment using various theoretical predictive mathematical models.

Electronic systems are complex structures with characteristics that may make accurate predictive analysis quite difficult. Further complicating predictive analysis is that the life-environment actually experienced by each particular electronic system is unique. Such individuality is particularly prevalent in the vibration-fatigue life of military and commercial avionic systems. Such predictive analysis, although effective, may not define the risk for all possible failures. Known in-service time, or known number of flights, missions, etc. may not accurately predict actual cumulative fatigue experienced by individual units. This may result in unanticipated failures or unnecessary anticipatory preventative maintenance and repair which may increase the associated life cycle costs. Accordingly, it is desirable to provide an in-situ monitoring system and method to determine if an electronic system is near the end of a vibration-fatigue life based on the life-environment actually experienced.

SUMMARY OF THE INVENTION

A monitoring system for an electronic component according to the present invention includes a calibrated micro-electro-mechanical structure (MEMS) matrix in communication with a controller. The MEMS include elements of various sizes which create a continuum of vibration-stress-resistant elements. The elements will flex in response to flexing of a printed circuit board due to mechanical vibration. The total accumulated flexure will initiate cracking and failure of the elements in order of the least-vibration-stress resistant element to the most-vibration-stress-resistant element. The controller monitors the continuity of the MEMS matrix to determine which elements of the MEMS matrix have failed to accurately determine the accumulated vibration stress experienced by the printed circuit board.

One monitoring system includes a MEMS matrix having a multitude of MEMS elements mounted in a cantilever arrangement.

Another MEMS matrix includes a multitude of MEMS elements mounted between a first support and a second support which are mounted to the printed circuit board to form a bridge-like structure.

Another monitoring system includes a MEMS matrix having a multitude of MEMS elements mounted between a first support and a second support. The MEMS matrix is mounted within a casing formed in part by the first support and the second support to encapsulate the monitoring system. A flexible membrane may be used to seal the bottom of the structure. A rod attached between the MEMS elements and the flexible membrane, or directly to the surface on which the sensor is mounted transfers the mechanical vibration of the flexible printed circuit board or surface on which the sensor is mounted through the casing opening to the MEMS elements such that failure thereof may be predicted as described above.

Another monitoring system includes a MEMS matrix having a multitude of MEMS elements arranged in a cubic or multi-dimensional matrix to receive vibrations from a multitude of directions.

The present invention therefore provide an in-situ monitoring system and method to determine if an electronic system is near the end of a vibration-fatigue life based on the life-environment actually experienced.

BRIEF DESCRIPTION OF THE DRAWINGS

The various features and advantages of this invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1A:
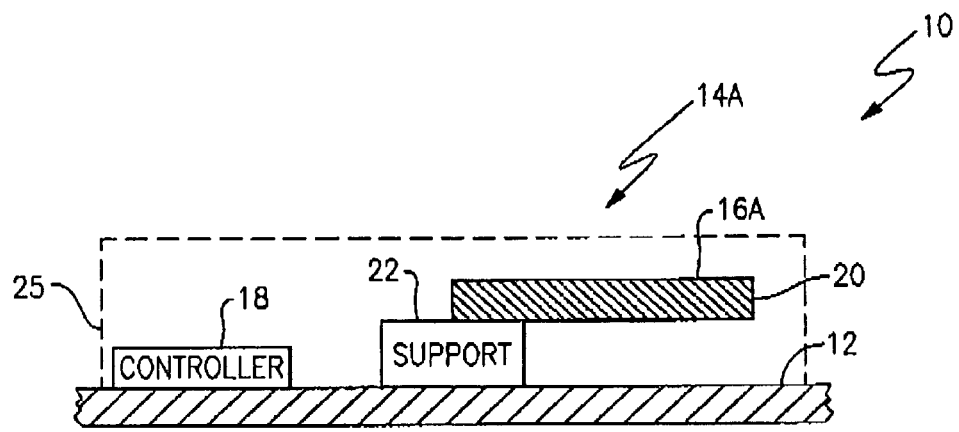
FIG. 1A is a side view of a monitoring system with cantilevered calibrated micro-electro-mechanical structures (MEMS) matrix.
Figure 1C:
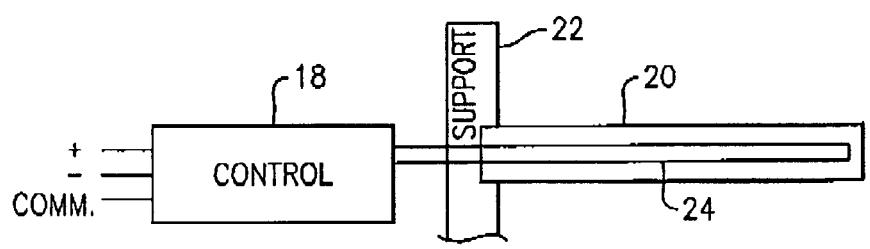
FIG. 1C is an expanded top view of one MEMS element and detection element therewith.
Figure 1B:
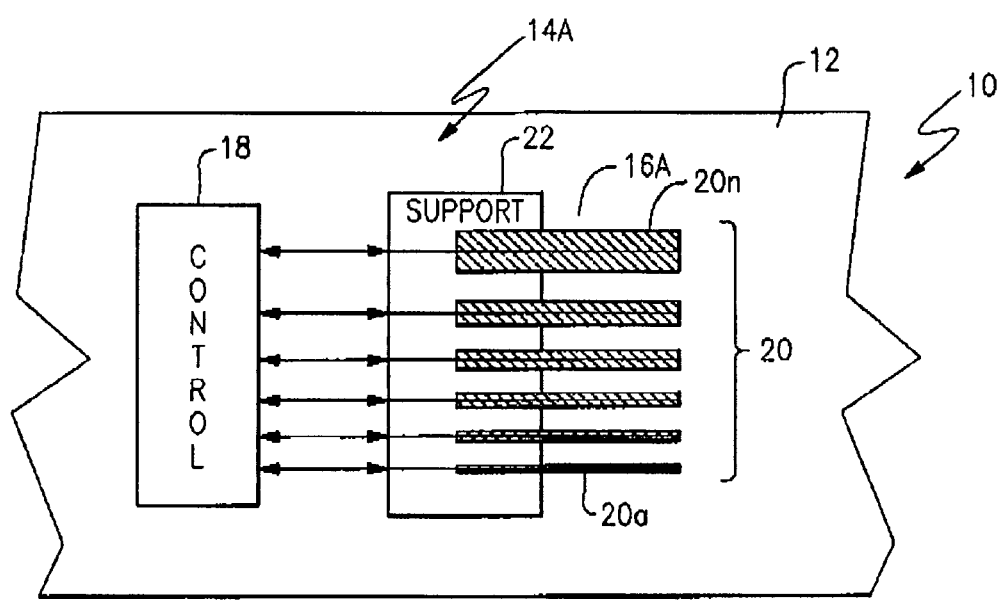
FIG. 1B is a top view of the monitoring system of FIG. 1A.

FIGS. 1A and 1B illustrate an electronic system 10 which generally includes a printed circuit board 12 having a monitoring system 14 mounted thereto. The monitoring system 14 is preferably packaged as an integrated sensor system which may be mounted to a rigid or flexible printed circuit board or other surface 12 within any electronic or mechanical system. Most preferably, the monitoring system 14 is particularly applicable to commercial and military avionics.

The monitoring system 14 generally includes a calibrated micro-electro-mechanical structures (MEMS) matrix 16 in communication with a controller 18. The MEMS 16 are preferably MEMS elements 20 of various sizes which create a continuum of vibration stress-resistant elements. It should be understood that elements of various widths, lengths, and depths will resist various levels of vibration stress. That is, each MEMS element 20 will resist failure until a predetermined vibration stress is experienced. The predetermined vibration stress is determined in a controlled environment. It should be understood that the number and configuration of the MEMS elements 20 will provide a desired fidelity. It should also be understood that although elements are disclosed in the illustrated embodiment, other shapes will likewise be usable with the present invention. The elements will flex in response to flexing of the printed circuit board or other surface 12 due to mechanical vibration. The total accumulated flexure will initiate cracking and failure of the elements in order of the least-vibration-stress resistant elements to the more-vibration stress-resistant element. The controller 18 monitors the continuity of the MEMS matrix 16 to determine which elements of the MEMS matrix 16 have failed such that the total amount of accumulated printed circuit board 12 flexure is accurately determined. The MEMS matrix 16 preferably includes a multitude of MEMS elements of various sizes to provide an accurate probabilistic estimate. The vibration-fatigue life based on the life-environment actually experienced by the particular printed circuit board (or other surface) 12 is thereby determined. It should be understood that the thermal-fatigue life based on the life-environment actually experienced by the particular printed circuit board (or other surface) 12 may also be determined by the monitoring system 14 utilizing MEMS elements which respond to thermal gradients and thermal fatigue cycles.

One monitoring system 14A includes a MEMS matrix 16A having a multitude of MEMS elements 20 mounted in a cantilever arrangement to a support 22 mounted to the printed circuit board 12. The MEMS elements 20 in the MEMS matrix 16A are arranged generally normal to the vibrations to be experienced by the printed circuit board 12 and include a range of sizes such that each of the MEMS elements 20 will progressively fail as the printed circuit board 12 experiences progressively increasing mechanical vibration. That is, each of the MEMS elements 20 in the MEMS matrix 16A will fail in order from the least-vibration-stress resistant MEMS element 20a to the most-vibration stress-resistant MEMS element 20n (FIG. 1B). It should be understood that multiple elements of having identical stress-resistant capacity may be utilized in the MEMS matrix 16 to provide additional accuracy in the probabilistic estimate as compared to that obtainable by single element of each size.

Each of the MEMS elements 20 in the MEMS matrix 16A includes a detection element 24 to provide communication of MEMS elements 20 failure to the controller 18 (only one shown in FIG. 1C). The MEMS elements 20 may be mounted using flip-chip or other direct mount techniques such that failure of the MEMS elements 20 is communicated through the detection element 24. The detection element 24 may be a detection element through which current is communicated or other element which is operable to identify a discontinuity or failure of each MEMS element 20. The controller 18 preferably includes a microprocessor which communicates with the multitude of detection elements 24 through a serial communication bus typically including a plus; minus; and communication line. It should be understood that any controller and detection element 24 which detects failure of the MEMS elements 20 will likewise be usable with the present invention.

Preferably, the MEMS matrix 16 is mounted within a casing 25 (FIG. 1A) to provide protection therefore. In response to mechanical vibration, the cantilevered MEMS elements 20 are vibrated until failure of the detection element 24 occurs. As the cantilevered MEMS elements 20 are free to vibrate and operate essentially as tuning forks, the cantilevered MEMS elements 20 will fail in order of the least-vibration-stress resistant MEMS element 20a to the most vibration-stress resistant MEMS element 20n within the MEMS matrix 16. As each MEMS element 20 fails in order, the associated detection element 24 fails thereby communicating a particular vibration stress level experienced to the controller 18. As each MEMS element 20 is calibrated through experimental testing to a particular vibration stress level, sequential failure of the MEMS elements 20 within the MEMS matrix 16 provide an accurate measure of the vibration-fatigue life of the printed circuit board 12 based on the life-environment actually experienced.

Figure 2A:
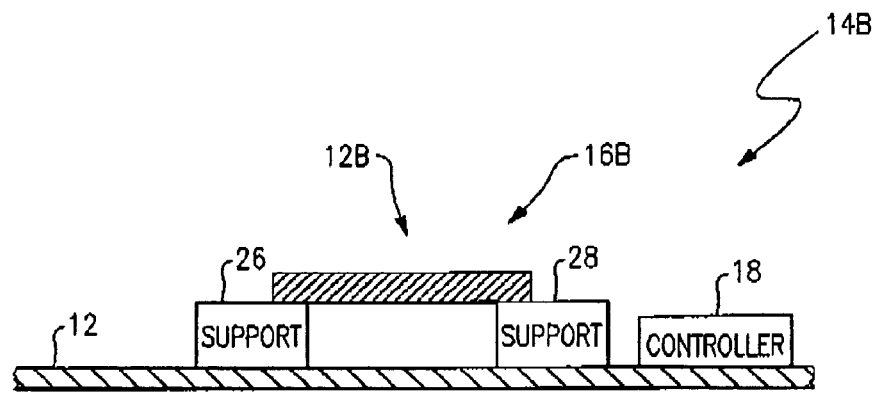
FIG. 2A is a side view of a monitoring system with a bridged calibrated micro-electro-mechanical structures (MEMS) matrix.
Figure 2B:
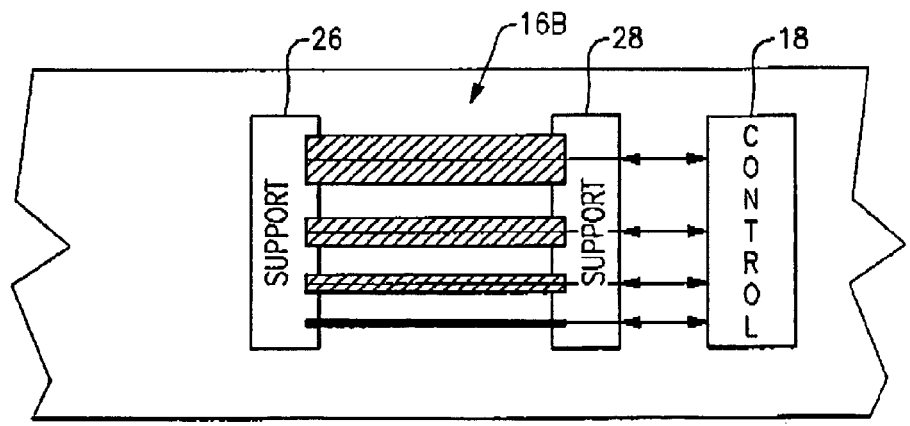
FIG. 2B is a top view of the monitoring system of FIG. 2A.

Referring to FIGS. 2A and 2B, another MEMS matrix 16B includes a multitude of MEMS elements 20 mounted between a first support 26 and a second support 28 which are mounted to the printed circuit board 12 to form a bridge-like structure. Each of the MEMS elements 20 also includes a detection element 24 described above to provide communication with the controller 18 such that as each MEMS element 20 fails, the detection element 24 fails to communicate the vibration level to the controller 18.

Figure 3:
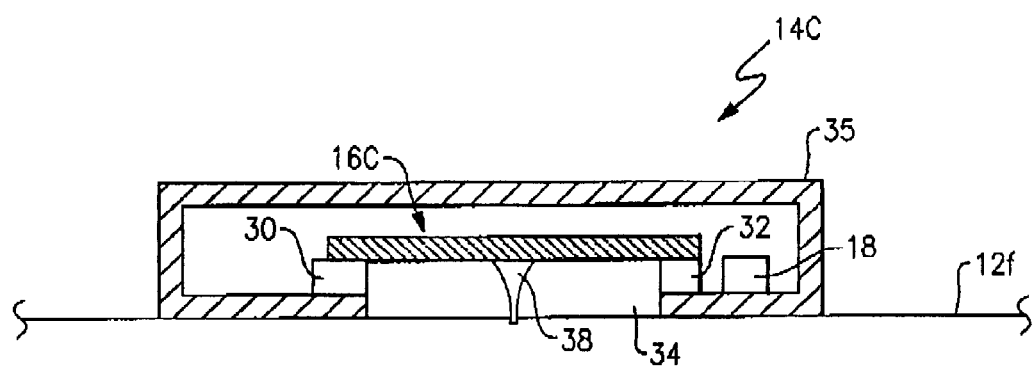
FIG. 3 is a side view of a monitoring system with calibrated micro-electro-mechanical structures (MEMS) matrix attached to a flexible circuit board.

Referring to FIG. 3, another monitoring system 14c includes a MEMS matrix 16C having a multitude of MEMS elements 20 mounted between a first support 30 and a second support 32 to span an opening 34 formed in a casing 36. The MEMS matrix 16C is preferably mounted within the casing 36 formed in part by the first support 30 and the second support 32. The casing 36 encapsulates the monitoring system 14c to permit attachment to a flexible printed circuit board 12F and provide a relatively fixed structure relative to which the flexible printed circuit board 12F may flex. That is, the flexible printed circuit board 12F is movable relative the casing 36 in response to mechanical vibration.

A rod 38 is attached between each of the MEMS elements 20 and the flexible membrane 12F through the opening 34. It should be understood that the term "rod" as utilized herein may include any attachment between the printed circuit board 12F and each MEMS element 20 intermediate the first support 30 and the second support 32. The rod 38 transfers the mechanical vibration of the surface on which the MEMS sensor is mounted through the flexible membrane 12F to the MEMS elements 20 such that failure thereof is determined as described above. Direct contact of the rod to the surface to be monitored is also possible. As each MEMS element 20 is calibrated through experimental testing to a particular vibration stress level, sequential failure of the MEMS elements 20 within the MEMS matrix 16c provide an accurate measure of the vibration-fatigue life experienced by the flexible printed circuit board 12F based on the life-environment actually experienced.

Figure 4A:
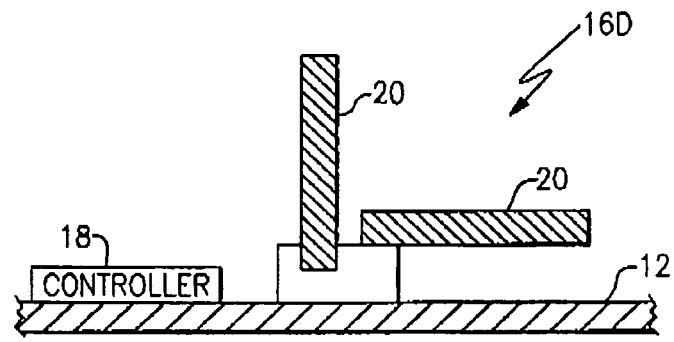
FIG. 4A is a side view of a monitoring system with a multi-dimensional calibrated micro-electro-mechanical structures (MEMS) matrix.
Figure 4B:
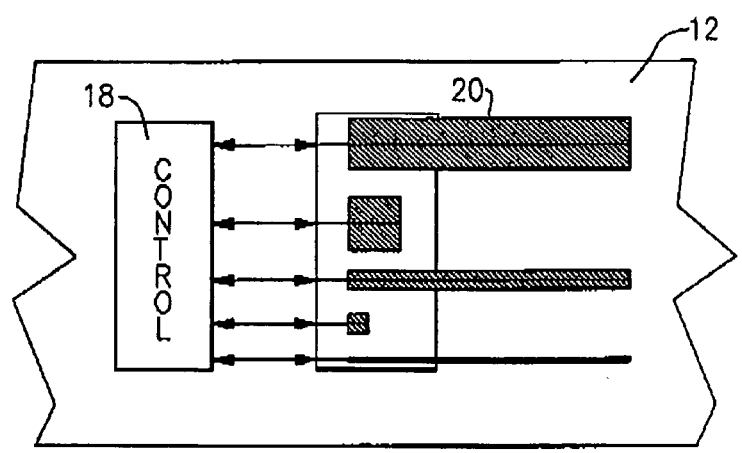
FIG. 4B is a top view of the monitoring system of FIG. 1A.

Referring to FIGS. 4A and 4B, another monitoring system 12 includes a MEMS matrix 16D having a multitude of MEMS elements 20 arranged in a cubic or multi-dimensional matrix. That is, the multitude of MEMS elements 20 are arranged to receive vibrations from a multitude of directions not just normal to the surface of the printed circuit board 12. By particularly arranging the MEMS matrix 16D in accordance with the expected mounting position of the electronic component, further fidelity may be provided to the measured vibration-fatigue life.

It should be understood that relative positional terms such as "forward," "aft," "upper," "lower," "above," "below," and the like are with reference to the normal operational attitude of the vehicle and should not be considered otherwise limiting.

It should be understood that although a particular component arrangement is disclosed in the illustrated embodiment, other arrangements will benefit from the instant invention.

Although particular step sequences are shown, described, and claimed, it should be understood that steps may be performed in any order, separated or combined unless otherwise indicated and will still benefit from the present invention.

The foregoing description is exemplary rather than defined by the limitations within. Many modifications and variations of the present invention are possible in light of the above teachings. The preferred embodiments of this invention have been disclosed, however, one of ordinary skill in the art would recognize that certain modifications would come within the scope of this invention. It is, therefore, to be understood that within the scope of the appended claims, the invention may be practiced otherwise than as specifically described. For that reason the following claims should be studied to determine the true scope and content of this invention.

What is claimed is:

1. A method of determining a vibration-fatigue life experienced by a printed circuit board comprising the steps of:
   (A) arranging a multitude of MEMS elements mounted to at least one support mounted to a printed circuit board, the multitude of MEMS elements forming a continuum from a least-vibration-stress resistant element to a most-vibration-stress resistant element;
   (B) detecting a failure of each of the multitude of MEMS elements, wherein the failure occurs at a pre-determined vibration stress; and
   (C) determining an accumulated vibration stress fatigue experienced by a printed circuit board using a controller in response to step (B).

2. A method as recited in claim 1, wherein said step (A) further comprises:
   (a) arranging the multitude of MEMS elements in a cantilever manner from a single support.

3. A method as recited in claim 1, wherein said step (A) further comprises:
   (a) arranging the multitude of MEMS elements in a bridge manner between a first support and a second support.

4. A method as recited in claim 1, wherein said step (A) further comprises:
   (a) arranging the multitude of MEMS elements in a multi-dimensional matrix.

5. The method as recited in claim 1, wherein the MEMS elements progressively fail in response to a mechanical vibration of the printed circuit board.

* * * * *